United States Patent [19]

Pfirmann et al.

[11] Patent Number: 5,488,152

[45] Date of Patent: Jan. 30, 1996

[54] PROCESS FOR THE PREPARATION OF 4-ALKOXY-3,5,6-TRIFLUORO-PHTHALIC ACIDS AND 3-ALKOXY-2,4,5-TRIFLUOROBENZOIC ACIDS

[75] Inventors: Ralf Pfirmann, Griesheim; Theodor Papenfuhs, Frankfurt, both of Germany

[73] Assignee: Hoechst Aktiengesellschaft, Frankfurt, Germany

[21] Appl. No.: 386,292

[22] Filed: Feb. 9, 1995

[30] Foreign Application Priority Data

Feb. 12, 1994 [DE] Germany .................. 44 04 519.0

[51] Int. Cl.⁶ .................................................. C07C 65/00
[52] U.S. Cl. ............................................................ 562/474
[58] Field of Search ................................................ 562/474

[56] References Cited

U.S. PATENT DOCUMENTS 5,380,926 1/1995 Fertel et al. ................. 562/474

FOREIGN PATENT DOCUMENTS

| 310569 | 12/1987 | European Pat. Off. . |
| 0271275 | 6/1988 | European Pat. Off. . |
| 1-268662 | 10/1989 | Japan . |
| 324131 | 4/1991 | Japan . |
| 279348 | 12/1991 | Japan . |
| 230344 | 8/1992 | Japan . |
| 320107 | 12/1993 | Japan . |
| 016656 | 1/1994 | Japan . |

OTHER PUBLICATIONS

Chem. Abst. 73:109544 1970.

*Primary Examiner*—Paul J. Killos
*Attorney, Agent, or Firm*—Connolly & Hutz

[57] ABSTRACT

The present invention relates to a process for the preparation of 4-alkoxy-3,5,6-trifluorophthalic acids of the formula

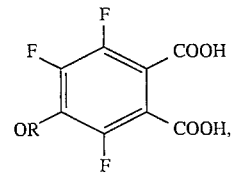

(1)

in which R is an alkyl radical having 1 to 5 carbon atoms which may be monofluorinated or polyfluorinated, a cycloalkyl radical having 3 to 5 carbon atoms in the ring which may be monofluorinated or polyfluorinated, or an araliphatic radical which may be monofluorinated or polyfluorinated, or, if desired, of 3-alkoxy-2,4,5-trifluorobenzoic acids of the formula

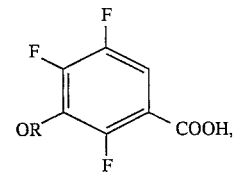

(2)

in which R is as defined above, which involves reacting tetrafluorophthalic acid or tetrafluorophthalic anhydride with an alcohol of the formula ROH in which R is as defined above and with a water-soluble base in water at elevated temperature, isolating the 4-alkoxy-3,5,6-trifluorophthalic acid formed and, if desired, decarboxylating the 4-alkoxy-3,5,6-trifluorophthalic acid in the presence of a basic solvent and, if desired, of an inert solvent at from 70° to 180° C., and isolating the 3-alkoxy-2,4,5-trifluorobenzoic acid formed.

30 Claims, No Drawings

PROCESS FOR THE PREPARATION OF 4-ALKOXY-3,5,6-TRIFLUORO-PHTHALIC ACIDS AND 3-ALKOXY-2,4,5-TRIFLUOROBENZOIC ACIDS

The present invention relates to a new, advantageous process for the preparation of 4-alkoxy-3,5,6-trifluorophthalic acids and, if desired, 3-alkoxy-2,4,5-trifluorobenzoic acids.

Both 4-alkoxy-3,5,6-trifluorophthalic acids and 3-alkoxy- 2,4,5-trifluorobenzoic acids are important intermediates for the preparation of new, highly active antibacterial agents from the series of the fluoroquinolonecarboxylic acids (JP 63 297 366; EP-A-0 443 498; EP-A-0 230 295; EP-A-0 241 206 and JP 63 316 757).

4-Alkoxy-3,5,6-trifluorophthalic acids are generally accessible only by way of a synthesis route which is complex and therefore of poor economy. Thus 4-methoxy-3,5,6-trifluorophthalic acid can be prepared as follows (N. Ishikawa et al., Nippon Kagaku Kaishi 1 (1976), 200–202 and EP-A-0 271 275): tetrafluorophthalic acid is reacted with methanol to give the corresponding dimethyl tetrafluorophthalate, a methoxygroup is then substituted for the fluorine atom in position 4, and thus dimethyl 4-methoxy-3,5,6-trifluorophthalate is obtained. Dimethyl 4-methoxy-3,5,6-trifluorophthalate is subsequently hydrolyzed to form 4-methoxy-3,5,6-trifluorophthalic acid. If desired, the 4-methoxy-3,5,6-trifluorophthalic acid can be converted by decarboxylation into 3-methoxy-2,4,5-trifluorobenzoic acid. Cf. also formula scheme A below.

(Formula scheme A)

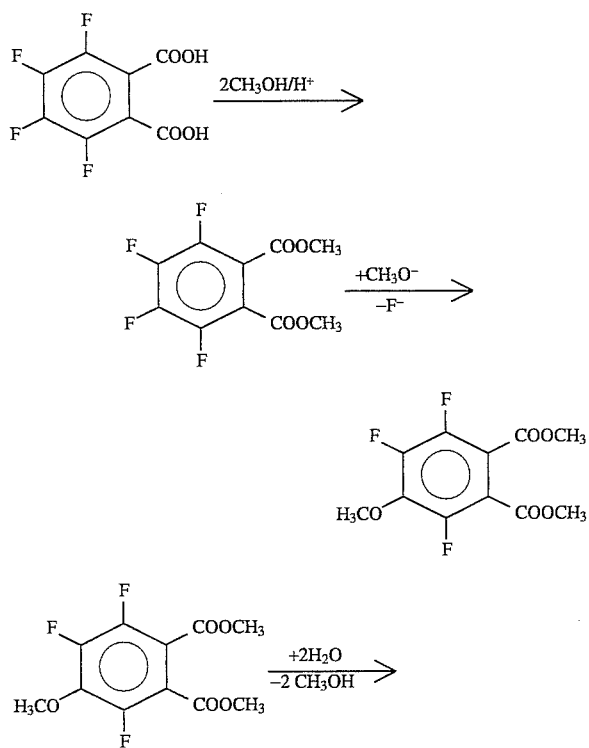

-continued
(Formula scheme A)

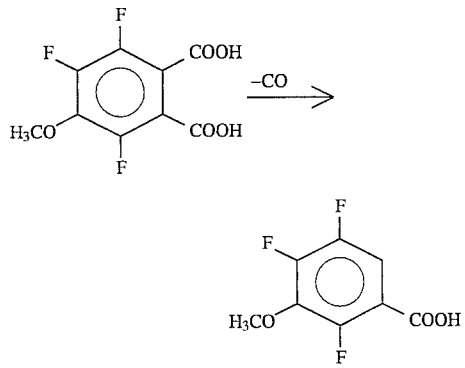

Other technically feasible and known processes for the preparation of 3-methoxy-2,4,5-trifluorobenzoic acid, 3-ethoxy-2,4,5-trifluorobenzoic acid, 3-propoxy-2,4,5-trifluorobenzoic acid and 3-butoxy-2,4,5-trifluorobenzoic acid each take place via 3-hydroxy-2,4,5-trifluorobenzoic acid, which in comparison is easily accessible and whose hydroxyl group in position 3 has to be subjected to selective alkylation (JP 01 268 662). 3-Hydroxy-2,4,5-trifluorobenzoic acid can be prepared in accordance with EP 271 275, as detailed below. Tetrafluorophthalic acid is reacted under the conditions of an aqueous-alkaline hydrolysis, with the substitution of a hydroxide group for the fluorine atom in position 4 to form 4-hydroxy- 3,5,6-trifluorophthalic acid. 4-Hydroxy-3,5,6-trifluorophthalic acid is subsequently converted by decarboxylation into 3-hydroxy-2,4,5-trifluorobenzoic acid. 3-Hydroxy-2,4,5-trifluorobenzoic acid is then reacted with an alkylating agent, for example dimethyl sulfate, to give the corresponding 3-alkoxy-2,4,5-trifluorobenzoic acid, e.g. 3-methoxy-2,4,5-trifluorobenzoic acid.

If, in accordance with this process, 4-alkoxy-3,5,6-trifluorophthalic acids are employed instead of 4-hydroxy-3,5,6-trifluorophthalic acid for decarboxylation in an aqueous acidic medium, there is little or no formation of the 3-alkoxy-2,4,5-trifluorobenzoic acids. The cause of this is the ether cleavage which takes place simultaneously under the conditions of the decarboxylation, in which case, from the 4-alkoxy-3,5,6-trifluorophthalic acids, it is in each case 3-hydroxy-2,4,5-trifluorobenzoic acid and not the corresponding 3-alkoxy-2,4,5-trifluorobenzoic acid which is formed (EP 271 275). The synthesis route described above can be seen from formula scheme B below:

(formula scheme B)

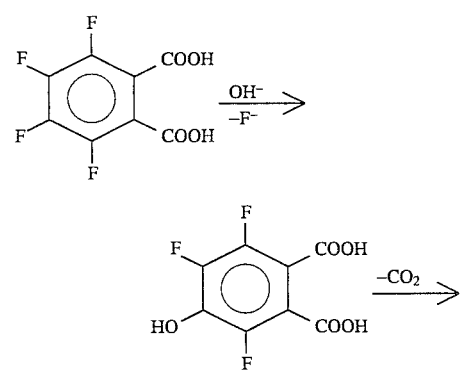

-continued
(formula scheme B)

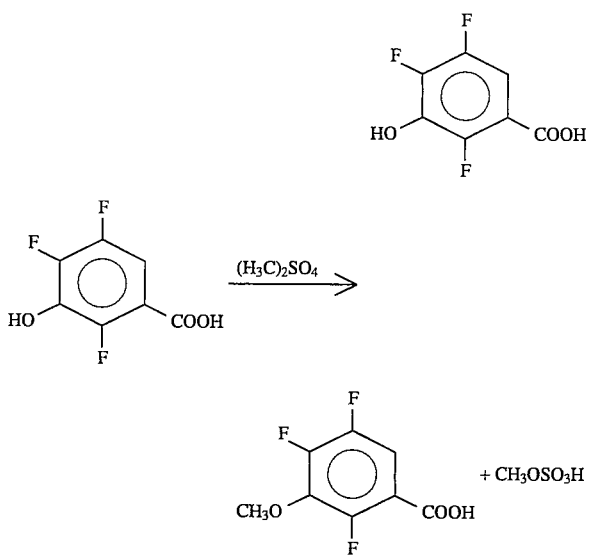

In comparison with the processes described in formula scheme B, the process of formula scheme A does indeed also give 4-alkoxy-3,5,6-trifluorophthalic acids, but because of the number of steps in the process it proves to be laborious. In addition, owing to the stoichiometry of the reaction, it requires not less than 3 moles of alcohol per mole of 4-alkoxy-3,5,6-trifluorophthalic acid or 3-alkoxy-2,4,5-trifluorobenzoic acid-to be prepared. Not less than 2 mol of alcohol are required in order to prepare, from the tetrafluorophthalic acid, the corresponding diesters. The two ester groups serve merely as protective groups and are subsequently removed by hydrolysis with the elimination of alcohol. From the point of view of valuable alcohols which are difficult to obtain this is an additional disadvantage, since it is not regarded as economic to subject ester groups synthesized from valuable alcohols to subsequent hydrolysis again.

With regard to the incorporation of alkoxy groups, the process of formula scheme B possesses a relatively small degree of variability, since the alkylating agents which are required for the synthesis and which contain the corresponding alkyl groups which are of interest for the preparation of the active substances are available only in a severely limited range. In addition, the handling of alkylating agents such as, for example, alkyl halides or dialkyl sulfates is highly problematic, since these substances are very toxic.

The object of the present invention is therefore to provide a process for the preparation not only of 4-alkoxy-3,5,6-trifluorophthalic acids but also, if desired, of 3-alkoxy-2,4,5-trifluorobenzoic acids, which is simplified relative to the prior art, does not have the abovementioned disadvantages and, in addition, can be employed as widely as possible.

This object is achieved by a process for the preparation of 4-alkoxy-3,5,6-trifluorophthalic acids of the formula

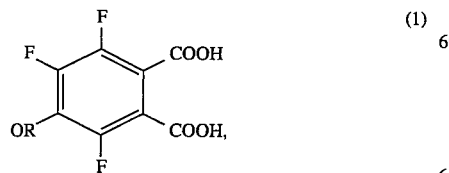
(1)

in which R is an alkyl radical having 1 to 5 carbon atoms which may be monofluorinated or polyfluorinated, a cycloalkyl radical having 3 to 5 carbon atoms in the ring which may be monofluorinated or polyfluorinated, or an araliphatic radical which may be monofluorinated or polyfluorinated, and, if desired, of 3-alkoxy-2,4,5-trifluorobenzoic acids of the formula

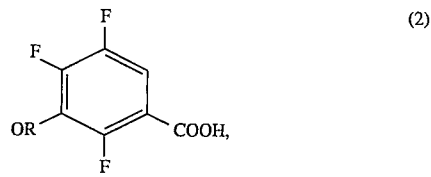
(2)

in which R is as defined above. The process comprises reacting tetrafluorophthalic acid or tetrafluorophthalic anhydride with an alcohol of the formula ROH in which R is as defined above and with a water-soluble base in water at elevated temperature, isolating the 4-alkoxy- 3,5,6-trifluorophthalic acid and, if desired, decarboxylating the 4-alkoxy-3,5,6-trifluorophthalic acid in the presence of a basic solvent and, if desired, of an inert solvent from 70° to 180° C., and isolating the 3-alkoxy-2,4,5-trifluorobenzoic acid formed.

The reaction sequence on which the process according to the invention is based can be seen from formula scheme C below.

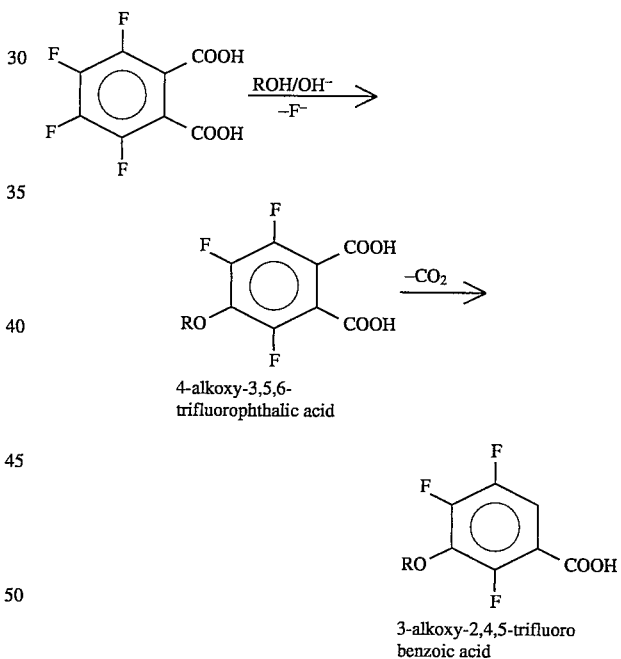

As evident simply by comparing the reaction sequences of formula schemes A and B, the process according to the invention is substantially simpler than the prior art. In addition it can be employed widely, since a large number of different alcohols are suitable for the first reaction step, namely the substitution of an alkoxy group for the fluorine atom in position 4. Moreover, only one mole of alcohol is consumed in the preparation of one mole of 4-alkoxy-3,5,6-trifluorophthalic acid or 3-alkoxy-2,4,5-trifluorobenzoic acid, respectively. Surprisingly, it is not necessary to protect the two carboxyl groups of the tetrafluorophthalic acid by esterification. The reaction proceeds with high selectivity and leads to a high yield of 4-alkoxy-3,5,6-trifluorophthalic acid. In addition to this the present invention ensures that the second reaction step, namely the decarboxylation of the 4-alkoxy-3,5,6-trifluorophthalic acid to give the 3-alkoxy-2,4,5-trifluorobenzoic acid, also has a high yield.

A further surprising feature is that the formation of secondary products, in particular from ether cleavage leading to the formation of 3-hydroxy-2,4,5-trifluorobenzoic acid, is avoided completely.

Suitable alcohols for reaction with tetrafluorophthalic acid or tetrafluorophthalic anhydride are, in a list which makes no claim to completeness, straight-chain or branched aliphatic alcohols, cycloaliphatic alcohols and araliphatic alcohols. The alcohol of the formula ROH which can be employed in the reaction is a primary or secondary alcohol, especially a primary alcohol.

Examples of alcohols of the formula ROH are methanol, ethanol, n-propanol, n-butanol, n-pentanol, cyclopropanol, hydroxymethylcyclopropane, fluoromethanol, difluoromethanol, trifluoromethanol, monofluoroethanol, difluoroethanol, trifluoroethanol, monofluoropropanol, monofluorobutanol, monofluorocyclopropanol, difluorocyclopropanol, benzyl alcohol, 4-fluorobenzyl alcohol or phenyl ethanol, especially methanol, ethanol, cyclopropanol, n-propanol, fluoromethanol, difluoromethanol, trifluoromethanol, monofluoroethanol, monofluorobutanol, benzyl alcohol or 4-fluorobenzyl alcohol.

In order to carry out the reaction it is advisable to employ from 1 to 100 mol, in particular from 20 to 80 mol and preferably from 40 to 60 mol of alcohol per mole of tetrafluorophthalic acid or tetrafluorophthalic anhydride.

The reaction takes place in the presence of a water-soluble base in water. The water-soluble base employed is a hydroxide, carbonate, phosphate, hydrogen phosphate or dihydrogen phosphate of an alkali metal or of an alkaline earth metal, or a mixture thereof. Highly suitable water-soluble bases include lithium hydroxide, lithium hydroxide hydrate, sodium hydroxide and potassium hydroxide.

It is usual to employ from 1 to 100 mol, in particular from 1.1 to 10 mol and preferably from 2 to 5 mol of base per mole of tetrafluorophthalic acid or tetrafluorophthalic anhydride.

The reaction takes place in the presence of water. It is usual to employ from 1 to 1500 mol, in particular from 10 to 300 mol and preferably from 25 to 200 mol of water per mole of tetrafluorophthalic acid or tetrafluorophthalic anhydride.

The reaction of tetrafluorophthalic acid or tetrafluorophthalic anhydride with the alcohol of the formula ROH and the water-soluble base in water takes place at elevated temperature, usually at from 25° to 150° C. In many cases it has proven adequate to allow the reaction to take place at from 50° to 120° C., especially from 60° to 100° C. At this point, however, it should be noted that the reaction temperature to be chosen depends to a certain extent on the reactivity of the alcohol employed in each case and on the other reaction conditions. It should be adapted correspondingly to the appropriate circumstances.

At the end of the reaction, an aqueous reaction mixture is obtained from which it is necessary to separate off the particular product desired. It is usual to distill off unreacted alcohol from the aqueous reaction mixture and to isolate the 4-alkoxy-3,5,6-trifluorophthalic acid by addition of acid and/or by extraction from the aqueous reaction mixture.

The aqueous reaction mixture which has been freed from unreacted alcohol is extracted using a water-insoluble organic solvent or the basic solvent. Suitable water-insoluble organic solvents are polar organic solvents, for example dialkyl ethers or esters of aliphatic carboxylic acids having 1 to 6 carbon atoms.

If it is intended to convert the 4-alkoxy-3,5,6-trifluorophthalic acid formed into the 3-alkoxy-2,4,5-trifluorobenzoic acid by decarboxylation, then it is advisable to extract the aqueous reaction mixture, which has been free from unreacted alcohol, using the basic solvent and to employ this mixture for subsequent processing. This procedure is particularly simple.

The basic solvent employed is an organic base, for example a straight-chain or branched aliphatic amine, a mono- or polysubstituted pyrrole, pyrrolidone, imidazole, imidazolidinone, pyridine, pyrimidine, quinoline, isoquinoline, an N,N-dialkylated carboxamide or mixtures of these compounds, especially a trialkylamine having 4 to 20, preferably 6 to 14, carbon atoms in the alkyl radical, mixtures of these trialkylamines, collidine, quinoline, N-methylpyrrolidone, N,N-dimethylacetamide, 1,3-dimethylimidazolidinone or mixtures of these compounds.

In a number of cases it may be useful to employ in addition a solvent which is inert under the conditions of the reaction. Inert solvents which are employed are aromatic hydrocarbons, mono- or polyhalogenated aromatic hydrocarbons or mixtures thereof. In a list which makes no claim to completeness, suitable inert solvents are toluene, ethylbenzene, mesitylene, o-xylene, m-xylene, p-xylene, technical-grade mixtures of isomeric xylenes, chlorobenzene, dichlorobenzene, trichlorobenzene, chlorotoluene, dichlorotoluene or mixtures thereof.

As already mentioned above, the decarboxylation is carried out at from 70° to 180° C. In many cases it has proven adequate to carry out the decarboxylation from 80° to 170° C., especially from 100° to 150° C.

Following decarboxylation the reaction mixture is extracted with an aqueous solution containing a base, the aqueous phase obtained is separated, the 3-alkoxy-2,4,5-trifluorobenzoic acid is precipitated by acidification and the precipitate is isolated by filtration. Bases which can be used, dissolved in water, are alkali metal hydroxides, and alkali metal carbonates, in particular lithium hydroxide, sodium hydroxide or potassium hydroxide. Following the separation of the aqueous phase, it is common to employ a mineral acid, for example hydrochloric acid, sulfuric acid or phosphoric acid, in an adequate quantity, i.e. up to a pH of from 0 to 3, in particular from 1 to 2.5, and to filter off the 3-alkoxy-2,4,5-trifluorobenzoic acid.

The examples which follow describe the invention without limiting it.

EXAMPLE 1

Reaction with methanol 4.4 g (20 mmol) of tetrafluorophthalic anhydride are dissolved in 6 g of water and 30 g of methanol, the temperature rises to 30° C. and the solution takes on a yellow coloration. 8.2 g (0.2 mol) of lithium hydroxide hydrate are added and the mixture is heated at reflux (65° C.) for 10 hours. After this time no further tetrafluorophthalic anhydride can be detected by GC analysis. 30 g of water are added and unreacted methanol (39 g) is distilled off completely up to a head temperature of 100° C. The mixture is then adjusted to a pH of 1 by addition of 30% strength hydrochloric acid and the colorless precipitate obtained is filtered off with suction. The aqueous phase is extracted twice with a mixture of in each case 20 g of 1,2-dichlorobenzene and 10 g of Hostarex A327 (a mixture of various aliphatic trialkyl amines having 6 to 14 carbon atoms in the alkyl radical). After this the aqueous phase contains no organic acids which are detectable by GC analysis. The extract phase is heated at 140° C. for 2 hours until the evolution of gas comes to an end (decarboxylation). After cooling the phase is rendered alkaline (pH≧11) using sodium hydroxide solution and is extracted several times with dichloromethane. The aqueous phase which remains is processed further by recovering the Hostarex A327 and the solvents by distillation. The aqueous phase is then reacidified (pH=1) and is extracted twice using in each case 20 g of methyl tert-butyl ether (MTBE). The extract is dried over $MgSO_4$ and filtered and the solvent is removed on a rotary evaporator, to leave 2.7 g (13.1 mmol, corresponding to 66%) of pale yellow powder which is shown by GC-MS to be methoxytrifluorobenzoic acid (GC purity>95%). It can be purified further by stirring out (recrystallization) from hot water.

EXAMPLE 2

Reaction with methanol

The procedure of Example 1 is followed but carrying out the extraction not with Hostarex A327 but instead, three times, with in each case 20 g of MTBE. The organic phase is dried over $MgSO_4$ and filtered and removal of the solvent leaves 3.8 g (15.2mmol, corresponding to 76%) of yellowish 4-methoxy-3,5,6-trifluorophthalic acid (purity according to GC>90%).

EXAMPLE 3

Reaction with ethanol 4.4 g (20 mmol) of tetrafluorophthalic anhydride are dissolved in 3 g of water and 30 g of ethanol, 4.2 g of lithium hydroxide hydrate are added, and the mixture is heated at reflux for 48 hours. Then 50 g of water are added and an ethanol/water mixture (31.9 g) is distilled off until a head temperature of 100° C. is reached. Subsequently a pH of 0.6 is established by adding 19 g of 30% strength hydrochloric acid, and the mixture is extracted using a mixture of 20 g of 1,2-dichlorobenzene and 10 g of Hostarex A327. The organic phase is dried over $MgSO_4$, heated at 140° C. for one hour until the evolution of gas comes to an end (decarboxylation) and then adjusted at 25° C. to a pH of 14 using 12.1 g of 35% strength sodium hydroxide solution. The mixture is extracted three times with in each case 50 g of dichloromethane, and the aqueous phase is adjusted to a pH of 0.7 by adding 9.4 g of 30% strength hydrochloric acid and extracted with MTBE. The mixture is dried over $MgSO_4$ and filtered, and removal of the solvent leaves 3.4 g (15.5 mmol, corresponding to 77%) of yellowish 3-ethoxy- 2,4,5-trifluorobenzoic acid (purity by GC>95%).

3-Ethoxy-2,4,5-trifluorobenzoic acid:

MS: m/e (%): 99 (8.8), 119 (7.8), 147 (6.5), 174 (5.1), 175 (98.2), 192 (100), 193 (6.2), 220 (23.4)

EXAMPLE 4

Reaction with ethanol

The procedure of Example 3 is followed but the 4-ethoxy-3,5,6-trifluorophthalic acid is isolated as described in Example 2, to give 4.6 g (17.4 mmol, corresponding to 87%) of 4-ethoxy-3,5,6-trifluorophthalic acid.

4-Ethoxy-3,5,6-trifluorophthalic acid:

MS: m/e (%): 78 (9.8) 98 (26.3), 117 (29), 146 (71.4), 174 (100), 175 (5.9), 218 (70.6), 246 (25.5, $(M-H_2O)^+$

EXAMPLE 5

Reaction with trifluoroethanol

An initial charge comprising a mixture of 7.6 g of water, 2.1 g of lithium hydroxide hydrate, 10 g of trifluoroethanol and 2.2 g (10 mmol) of tetrafluorophthalic anhydride is heated at 70° C. for 96 hours, after which the content of tetrafluorophthalic anhydride has fallen to below 1% (GC). The procedure described in Example 3 is then followed to give 1.4 g (5.1 mmol, corresponding to 51%) of 3-trifluoroethoxy-2,4,5-trifluorobenzoic acid.

EXAMPLE 6

Reaction with trifluoroethanol

The procedure of Example 5 is followed but without the decarboxylation and with isolation of the phthalic acid as described in Example 2 to give 2.2 g (6.9 mmol, corresponding to 69%) of 4-trifluoroethoxy-3,5,6-trifluorophthalic acid as a pale yellowish solid.

This solid can be decarboxylated by taking it up in Hostarex A 327 (324) and heating, with the subsequent procedure being as indicated in Example 5. 2,2,3,3-Tetrafluoropropanol can be reacted in an entirely analogous manner. 4-Trifluoroethoxy-3,5,6-trifluorophthalic acid:

MS: m/e [%]: 79 (14), 83 (7), 98 (12), 117 (42), 129 (14), 145 (17), 146 (11), 157 (5), 159 (30), 228 (100), 229 (8), 256 (89), 281 (13), 300 ($M-H_2O$), 90), 301 (9)

EXAMPLE 7

Reaction with 4-fluorobenzyl alcohol 8.4 g (0.15 mol) of potassium hydroxide are dissolved in 30 g of water, and 6.6 g (30mmol) of tetrafluorophthalic anhydride and 30 g (0.238 mol) of 4-fluorobenzyl alcohol are added. The mixture is heated at 100° C. for 12 hours after which the procedure as described in Example 2 is followed. It is advantageous not to allow the pH to fall below 3 prior to the extraction steps. This method gives 4.2 g (14 mmol, corresponding to 47%) of (4-fluorobenzyloxy) trifluorobenzoic acid (purity 80–85%).

We claim:

1. A process for the preparation of a 4-alkoxy-3,5,6-trifluorophthalic acid of the formula

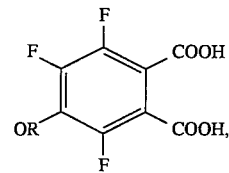

(1)

in which R is an alkyl radical having 1 to 5 carbon atoms which may be monofluorinated or polyfluorinated, a cycloalkyl radical having 3 to 5 carbon atoms in the ring which may be monofluorinated or polyfluorinated, or an araliphatic radical which may be monofluorinated or polyfluorinated,

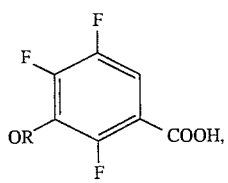

which comprises reacting tetrafluorophthalic acid or tetrafluorophthalic anhydride with an alcohol of the formula ROH in which R is as defined above and with a water-soluble base in water at elevated temperature, and isolating the 4-alkoxy-3,5,6-trifluorophthalic acid formed.

2. The process as claimed in claim 1, wherein the alcohol of the formula ROH employed is a primary alcohol.

3. The process as claimed in claim 1, wherein the alcohol of the formula ROH employed is methanol, ethanol, n-propanol, n-butanol, n-pentanol, cyclopropanol, hydroxymethylcyclopropane, fluoromethanol, difluoromethanol, trifluoromethanol, monofluoroethanol, difluoroethanol, trifluoroethanol, monofluoropropanol, monofluorobutanol, monofluorocyclopropanol, difluorocyclopropanol, benzyl alcohol, 4-fluorobenzyl alcohol or phenyl ethanol.

4. The process as claimed in claim 1 wherein the alcohol of the formula ROH employed is methanol, ethanol, cyclopropanol, n-propanol, fluoromethanol, difluoromethanol, trifluoromethanol, monofluoroethanol, monofluorobutanol, benzyl alcohol or 4-fluorobenzyl alcohol.

5. The process as claimed in claim 1, wherein from 1 to 100 mol of alcohol are employed per mole of tetrafluorophthalic acid or tetrafluorophthalic anhydride.

6. The process as claimed in claim 1, wherein a hydroxide, carbonate, phosphate, hydrogen phosphate or dihydrogen phosphate of an alkali metal or of an alkaline earth metal or a mixture thereof is employed as water-soluble base.

7. The process as claimed in claim 1, wherein lithium hydroxide, lithium hydroxide hydrate, sodium hydroxide or potassium hydroxide is employed as water-soluble base.

8. The process as claimed in claim 1, wherein from 1 to 100 mol of base are employed per mole of tetrafluorophthalic acid or tetrafluorophthalic anhydride.

9. The process as claimed in claim 1, wherein from 1 to 1500 mol of water are employed per mole of tetrafluorophthalic acid or tetrafluorophthalic anhydride.

10. The process as claimed in claim 1, wherein the tetrafluorophthalic acid or the tetrafluorophthalic anhydride is reacted with the alcohol at from 25° to 150° C.

11. The process as claimed in claim 1, wherein unreacted alcohol is distilled off from the aqueous reaction mixture and the 4-alkoxy-3,5,6-trifluorophthalic acid is isolated by addition of acid and/or by extraction from the aqueous reaction mixture.

12. The process as claimed in claim 1, wherein the aqueous reaction mixture is extracted with a water-insoluble organic solvent or with a basic solvent.

13. A process as claimed in claim 1, further comprising the steps of decarboxylating the 4-alkoxy-3,5,6-trifluorophthalic acid in the presence of a basic solvent, at a temperature of from 70° to 180° C. to form a 3-alkoxy-2,4,5-trifluorobenzoic acid, of the formula (2)

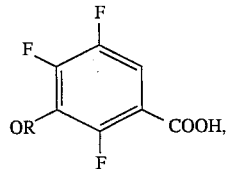

and isolating the alkoxy-2,4,5-trifluorobenzoic acid formed.

14. The process as claimed in claim 13, wherein a straight-chain or branched aliphatic amine, an optionally mono- or polyalkyl- substituted pyrrole, pyrrolidone, imidazole, imidazolidinone, pyridine, pyrimidine, quinoline, isoquinoline, an N,N-dialkylated carboxamide or a mixture of these compounds is employed as basic solvent.

15. The process as claimed in claim 13, wherein a trialkylamine having 4 to 20 carbon atoms in the alkyl radical, a mixture of these trialkylamines, collidine, quinoline, N-methylpyrrolidone, N,N-dimethylacetamide, 1,3-dimethylimidazolidinone or a mixture of these compounds is employed as basic solvent.

16. The process as claimed in claim 13, wherein decarboxylation is carried out in the presence of a basic solvent and an inert solvent.

17. The process as claimed in claim 16, wherein an aromatic hydrocarbon, a mono- or polyhalogenated aromatic hydrocarbon or a mixture thereof is employed as inert solvent.

18. The process as claimed in claim 16, wherein toluene, ethylbenzene, mesitylene, oxylene, m-xylene, p-xylene, a technical-grade mixture of isomeric xylenes, chlorobenzene, dichlorobenzene, trichlorobenzene, chlorotoluene, dichlorotoluene or a mixture thereof is employed as inert solvent.

19. The process as claimed in claim 13, wherein decarboxylation is carried out at from 80° C. to 170° C.

20. The process as claimed in claim 1, wherein the reaction mixture is extracted with an aqueous solution of a base after decarboxylation, the aqueous phase is separated, the 3-alkoxy-2,4,5-trifluorobenzoic acid is precipitated by acidification, and the precipitate is isolated by filtration.

21. The process as claimed in claim 1, wherein from 20 to 80 mol of alcohol are employed per mol of tetrafluorophthalic acid or tetrafluorophthalic anhydride.

22. The process as claimed in claim 1, wherein from 40 to 60 mol of alcohol are employed per mol of tetrafluorophthalic acid or tetrafluorophthalic anhydride.

23. The process as claimed in claim 1, wherein from 1.1 to 10 mol of base are employed per mol of tetrafluorophthalic acid or tetrafluorophthalic anhydride.

24. The process as claimed in claim 1, wherein from 2 to 5 mol of base are employed per mol of tetrafluorophthalic acid or tetrafluorophthalic anhydride.

25. The process as claimed in claim 1, wherein from 10 to 300 mol of water are employed per mol of tetrafluorophthalic acid or tetrafluorophthalic anhydride.

26. The process as claimed in claim 1, wherein from 25 to 200 mol of water are employed per mol of tetrafluorophthalic acid or tetrafluorophthalic anhydride.

27. The process as claimed inn claim 1, wherein the tetrafluorophthalic acid or the tetrafluorophthalic anhydride is reacted with the alcohol at a temperature of from 50° to 120° C.

28. The process as claimed inn claim 1, wherein the tetrafluorophthalic acid or the tetrafluorophthalic anhydride is reacted with the alcohol at a temperature of from 60° to 100° C.

29. The process as claimed in claim 13, wherein decarboxylation is carried out at a temperature of from 100° to 150° C.

30. The process as claimed in claim 12, wherein the water-insoluble organic solvent is a dialkyl ether or an ester of an aliphatic carboxylic acid having 1 to 6 carbon atoms.

* * * * *

UNITED STATES PATENT AND TRADEMARK OFFICE
CERTIFICATE OF CORRECTION

PATENT NO. : 5,488,152
DATED : January 30, 1996
INVENTOR(S) : Ralf Pfirmann and Theodor Papenfuhs It is certified that error appears in the above-indentified patent and that said Letters Patent is hereby corrected as shown below:

In claim 1 (column 9, line 5) the formula (2) should be deleted.

In claim 18 (column 10, line 22) "oxylene" should read --o-xylene--.

In claim 27 (column 10, line 51) the word "inn" should read --in--.

In claim 28 (column 10, line 55) the word "inn" should read --in--.

Signed and Sealed this

Fourteenth Day of May, 1996

*Attest:*

BRUCE LEHMAN

*Attesting Officer*     *Commissioner of Patents and Trademarks*